United States Patent
Wang et al.

(10) Patent No.: US 11,961,245 B2
(45) Date of Patent: Apr. 16, 2024

(54) METHOD AND APPARATUS FOR PERFORMING IMAGE GUIDANCE, MEDICAL EQUIPMENT, AND COMPUTER-READABLE STORAGE MEDIUM

(71) Applicant: OUR UNITED CORPORATION, Xi'an (CN)

(72) Inventors: Zhongya Wang, Xi'an (CN); Daliang Li, Xi'an (CN); Hao Yan, Xi'an (CN); Jiuliang Li, Xi'an (CN)

(73) Assignee: Our United Corporation, Xi'an (CN)

( * ) Notice: Subject to any disclaimer, the term of this patent is extended or adjusted under 35 U.S.C. 154(b) by 267 days.

(21) Appl. No.: 17/290,715

(22) PCT Filed: Oct. 30, 2018

(86) PCT No.: PCT/CN2018/112586
§ 371 (c)(1),
(2) Date: Apr. 30, 2021

(87) PCT Pub. No.: WO2020/087257
PCT Pub. Date: May 7, 2020

(65) Prior Publication Data
US 2022/0020164 A1    Jan. 20, 2022

(51) Int. Cl.
*G06T 7/00* (2017.01)
*G06T 7/38* (2017.01)

(52) U.S. Cl.
CPC ...... *G06T 7/38* (2017.01); *G06T 2207/10088* (2013.01)

(58) Field of Classification Search
CPC ... G06T 7/38; G06T 2207/10088; G06T 7/30; G06T 2207/10081; G06T 2207/10116; G06T 17/00; A61N 5/1049; G06F 3/0482
See application file for complete search history.

(56) References Cited

U.S. PATENT DOCUMENTS

2008/0212858 A1* 9/2008 Boese ............... G06T 7/38
382/130
2012/0314923 A1* 12/2012 Barnhorst ......... A61B 34/25
382/128
(Continued)

FOREIGN PATENT DOCUMENTS

| CN | 100998512 A | 7/2007 |
| CN | 101234020 A | 8/2008 |

(Continued)

OTHER PUBLICATIONS

International search report of PCT application No. PCT/CN2018/112586 dated Jul. 25, 2019.
(Continued)

*Primary Examiner* — Van D Huynh
(74) *Attorney, Agent, or Firm* — Knobbe, Martens, Olson & Bear LLP

(57) ABSTRACT

Provided is a method for performing image guidance, including: acquiring a 3D magnetic resonance (MR) image of a target individual, wherein at least one region range of an object of interest is marked in the 3D MR image; acquiring a reference 3D image of the target individual, wherein the reference 3D image is a 3D-reconstructed computed tomography (CT) image; performing a 3D-3D registration on the 3D MR image and the reference 3D image, so as to mark each region range of the object of interest in the reference 3D image; and performing image guidance on the basis that the reference 3D image is adopted to characterize an initial position state.

20 Claims, 3 Drawing Sheets

(56) References Cited

U.S. PATENT DOCUMENTS

| | | | | |
|---|---|---|---|---|
| 2013/0235969 | A1* | 9/2013 | Winter | A61N 5/1079 378/4 |
| 2014/0072196 | A1* | 3/2014 | Hwang | G06T 7/0016 382/130 |
| 2015/0217136 | A1* | 8/2015 | Stanescu | G01R 33/567 324/309 |
| 2017/0148180 | A1* | 5/2017 | Elenbaas | G06T 7/11 |
| 2017/0228896 | A1 | 8/2017 | Yu et al. | |
| 2017/0301080 | A1* | 10/2017 | Yan | G06T 7/337 |
| 2018/0025466 | A1 | 1/2018 | Mazurkewitz et al. | |
| 2019/0015060 | A1* | 1/2019 | Weiss | A61B 5/055 |
| 2019/0220986 | A1* | 7/2019 | Magro | A61B 6/032 |
| 2020/0297431 | A1* | 9/2020 | Cameron | A61B 6/487 |
| 2022/0015686 | A1* | 1/2022 | Asaad | A61B 5/7246 |

FOREIGN PATENT DOCUMENTS

| | | |
|---|---|---|
| CN | 102232835 A | 11/2011 |
| CN | 103932796 A | 7/2014 |
| CN | 104637061 A | 5/2015 |
| CN | 105139442 A | 12/2015 |
| CN | 105488804 A | 4/2016 |
| CN | 106934807 A | 7/2017 |
| CN | 107209240 A | 9/2017 |
| CN | 108701220 A | 10/2018 |
| CN | 108711187 A | 10/2018 |
| EP | 2818116 A1 | 12/2014 |
| WO | 2009109874 A1 | 9/2009 |

OTHER PUBLICATIONS

Jianrong Dai, et al; Realization of image-guided radiotherapy; China J Radiat Oncol, Mar. 2006, vol. 15, No. 2.

Xiaogang Du, et al; Generation Algorithm of Digital Reconstruction Radiographs Based on CUDA; Computer Science, vol. 42, No. 2, Feb. 2015.

China National Intellectual Property Administration, First office action of Chinese application No. 201880031818.6 dated Mar. 24, 2023, which is foreign counterpart application of this US application.

Yandong Lian et al., A comparative study of 3D-CBCT and 4D-CBCT based image-guided radiotherapy for lung cancer, Modern Practical Medicine, vol. 05, May 20, 2017, entire document.

Dequan Xu et al., Application of image guided radiation therapy technology in patients with rectal cancer treated with intensity modulated radiation therapy technology before operation, Journal of Jilin University ( Medicine Edition), vol. 42 No. 6, Nov. 28, 2016, entire document.

China National Intellectual Property Administration, Second office action of Chinese application No. 201880031818.6 dated Aug. 9, 2023, which is foreign counterpart application of this US application.

Yaping Xu et al., Thoracic Radiation Oncology Management Decisions, Military Medical Science Press, Dec. 31, 2013, p. 11.

Kailiang Wu, Clinical Oncology Radiotherapy, Shanghai: Fudan University Press, Dec. 31, 2017, pp. 54-58.

China National Intellectual Property Administration, Notification to grant patent right for invention of Chinese application No. 201880031818.6 issued on Feb. 1, 2024, which is foreign counterpart application of this US application.

Sureerat Reaungamornrat et al., Mind Demons: Symmetric Diffeomorphic Deformable Registration of MR and CT for Image-Guided Spine Surgery, IEEE Transactions on Medical Imaging, Dec. 31, 2016.

* cited by examiner

METHOD AND APPARATUS FOR PERFORMING IMAGE GUIDANCE, MEDICAL EQUIPMENT, AND COMPUTER-READABLE STORAGE MEDIUM

This application is a US national phase application of international application No. PCT/CN2018/112586, filed on Oct. 30, 2018 and entitled "IMAGE GUIDANCE METHOD AND DEVICE, AND MEDICAL EQUIPMENT AND COMPUTER READABLE STORAGE MEDIUM", the content of which is incorporated by reference herein in its entirety.

TECHNICAL FIELD

The present disclosure relates to the field of medical imaging, and in particular, relates to a method and apparatus for performing image guidance, medical equipment, and a computer-readable storage medium.

BACKGROUND

The movement of a target volume may cause a focus position of a treatment beam to deviate from a position of the target volume in one treatment fractionation during radiotherapy. To address this problem, an image guidance technology can be adopted to determine and correct the deviation between the focus position of the treatment beam and the position of the target volume based on the images acquired in real time.

SUMMARY

The present disclosure provides a method and apparatus for performing image guidance, medical equipment, and a computer-readable storage medium.

According to a first aspect of the present disclosure, a method for performing image guidance is provided. The method includes:

acquiring a 3D magnetic resonance (MR) image of a target individual, wherein at least one region range of an object of interest is marked in the 3D MR image;

acquiring a reference 3D image of the target individual, wherein the reference 3D image is a 3D-reconstructed computed tomography (CT) image;

performing a 3D-3D registration on the 3D MR image and the reference 3D image, so as to mark each region range of the object of interest in the reference 3D image; and performing image guidance on the basis that the reference 3D image is adopted to characterize an initial position state.

In a possible implementation, before performing the image guidance on the basis that the reference 3D image is adopted to characterize the initial position state, the method further includes:

outputting a registration result of the 3D-3D registration, so as to correct a setup error between the MR image and the reference 3D image.

In a possible implementation, before outputting the registration result of the 3D-3D registration, so as to correct the setup error between the MR image and the reference 3D image, the method further includes:

reacquiring the reference 3D image of the target individual in response to that registration precision of the registration result does not satisfy an application condition.

In a possible implementation, the reference 3D image is a 3D-reconstructed cone beam computed tomography (CBCT) image; and before performing the 3D-3D registration on the 3D MR image and the reference 3D image, so as to mark each region range of the object of interest in the reference 3D image, the method further includes:

removing artifacts in the reference 3D image.

In a possible implementation, performing the image guidance on the basis that the reference 3D image is adopted to characterize an initial position state includes:

acquiring X-ray transmission images collected at two different angles;

performing a 2D-3D registration on the reference 3D image and the X-ray transmission images collected at the two different angles; and outputting a registration result of the 2D-3D registration, so as to correct a relative positional deviation of the target individual among the reference 3D image and the X-ray transmission images collected at the two different angles.

According to a second aspect of the present disclosure, an apparatus for performing image guidance is further provided. The apparatus includes: a processor and a memory storing program instructions therein, wherein the processor is configured to call the program instructions in the memory to execute any foregoing image guidance method.

According to a third aspect of the present disclosure, medical equipment is further provided. The medical equipment includes a processor and a memory storing program instructions therein, wherein the processor is configured to call the program instructions in the memory to execute any foregoing image guidance method.

According to a fourth aspect of the present disclosure, a computer-readable storage medium is further provided. The computer-readable storage medium stories a computer program therein, wherein the computer program includes program instructions, and the program instructions, when executed by a processor, causes the processor to execute any foregoing image guidance method.

DETAILED DESCRIPTION

In order to describe the principles and advantages of the present disclosure more clearly, the implementations of the present disclosure are further described in detail hereinafter with reference to the accompanying drawings. Apparently, the described embodiments are merely some rather than all of the embodiments of the present disclosure. Unless otherwise defined, the technical terms and scientific terms used in the present disclosure have the same meaning as how they are generally understood by persons of ordinary skill in the art to which the present disclosure pertains. Terms such as "first" and "second" used in the present disclosure are only used to distinguish different components and do not intend to indicate any order, number or importance.

During real-time image guidance, it generally requires the images used for characterizing an initial position state and a current position state of a focus to be acquired by a same or similar type of imaging technique, such as the X-ray transmission imaging technique and the computed tomography (CT) imaging technique that are both based on the X-ray radiation. In this way, an accurate and fast image registration can be implemented, and the foregoing positional deviation can be determined in real time.

As compared with other imaging techniques, magnetic resonance imaging (MRI) technique can obtain images that show the distribution of soft tissues more clearly, which is advantageous for the accurate positioning of a focus. Therefore, the MRI technique has a promising application prospect in the field of image guidance. However, as the imaging process of MRI is relatively time consuming and it is impossible to perform an accurate and fast image registration on a digital projection image generated by the MRI and an X-ray transmission image photographed in real time due to the imaging principle of the MRI, it is very difficult to apply the MRI technique to a real-time image guidance process in practice.

Figure 1:
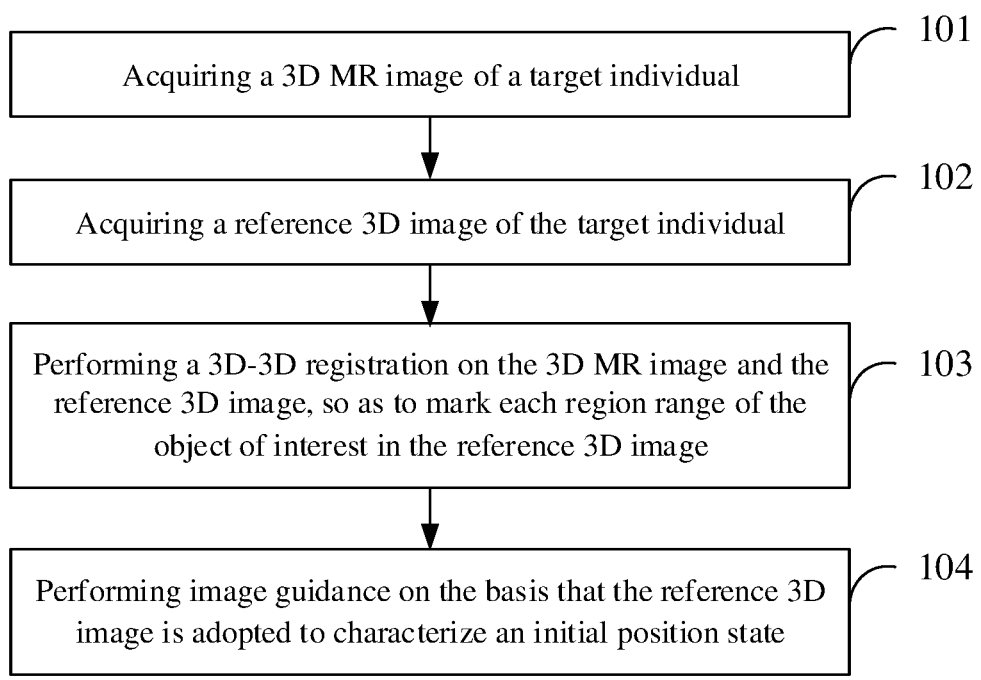
FIG. 1 is a schematic flowchart showing a method for performing image guidance according to an embodiment of the present disclosure.

FIG. 1 is a schematic flowchart showing a method for performing image guidance according to an embodiment of the present disclosure. Referring to FIG. 1, the method for performing image guidance includes the following steps.

In step 101, a 3D MR image of a target individual is acquired, where at least one region range of an object of interest is marked in the 3D MR image.

In step 102, a reference 3D image of the target individual is acquired, where the reference 3D image is a 3D-reconstructed CT image.

In step 103, a 3D-3D registration is performed on the 3D MR image and the reference 3D image, so as to mark each region range of the object of interest in the reference 3D image.

In step 104, image guidance is performed on the basis that the reference 3D image is adopted to characterize an initial position state.

It needs to be noted that, the method in the embodiments of the present disclosure is applicable to any medical activity including image guidance, for example, image-guided radio therapy (IGRT), brain tumor excision surgery or other surgery involving image guidance, or the like. It should be understood that the target individual refers to an object on which these medical activities are implemented, for example, a patient to be treated with radiotherapy or surgery. In an example, the method for performing image guidance may be implemented as software installed within medical equipment (for example, radiotherapy equipment, image-guided medical equipment, an operating table, or the like), so that an image guidance process can be implemented during the medical activity. On this basis, the 3D MR image may be a 3D image acquired by mainly using an MRI technique to perform imaging on the target individual. The 3D MR image may be acquired by the medical equipment from imaging equipment through communication connection, or it may be acquired from the imaging process of the medical equipment per se. The reference 3D image may be 3D image(s) derived from a 3D reconstruction performed on images obtained by imaging the target individual through imaging techniques such as CT-based imaging techniques. The reference 3D image may be acquired after the foregoing medical equipment receives image(s) from imaging equipment through communication connection and performs processing, or it may be received by the foregoing medical equipment from image processing equipment through communication connection, or it may be acquired after the medical equipment per se performs imaging and processing. The CT-based imaging techniques may be a cone beam CT (CBCT) technique, a single slice helical CT (SSCT) technique, a multi-slice helical CT (MSCT) technique, or the like.

It should be understood that, the region range of the object of interest is a certain range of region manually selected by a user in an MR image, and may for example be a region range of a focus under radiotherapy, a position of a specified dissection point, or a region range of a tumor and blood vessel tissue around the tumor in a brain tumor excision surgery, or the like. In an example, a user can select each region range of the object of interest by performing a selection operation on the medical equipment after the medical equipment receives the 3D MR image, displays it and provides a region selection tool on it. In another example, the medical equipment receives from the imaging equipment an MR image in which each region range of the object of interest has been marked. Since the MR image can clearly show the characteristics of the distribution of soft tissues, the region range(s) of the object of interest marked in the MR image can have a more accuracy than other types of images.

It should be further understood that an image registration refers to a process of performing a spatial transformation (or a series of spatial transformations) on an image, so as to make points on the image spatially consistent with corresponding points on another image. That is, the 3D-3D registration refers to a process of making a spatial transformation or a series of spatial transformations by means of which the MR image can overlap the reference 3D image. It needs to be noted that, the 3D-3D registration may be performed only within a spatial region of interest (ROI) concerned by the medical activity, so as to reduce an algorithm cost. Similarly, the MR image and the reference 3D image may be collected only directed to the spatial ROI concerned by the medical activity, so as to shorten an imaging time and reduce an exposure dose. It needs to be further noted that the result of the image registration may be represented as relative position coordinates of the same positioning point(s) (or referred to as the same-name points, which may, for example, include dissection point(s) or image feature point(s)) between images, or may be alternatively represented as a transform matrix between images, or may otherwise be represented as a form showing the correspondence of each same-name image region between images. The result of the image registration is not limited thereto. Based on the registration result of the 3D-3D registration, at least one region range of the object of interest in an MR image can be marked in the reference 3D image. It can be understood that even if the object of interest showed in the reference 3D image is not clear or no object of interest is showed at all, as long as the registration precision meets the application requirement, the marking of each region range of the object of interest can be accomplished in the reference 3D image based on the registration result.

It should be further understood that the initial position state refers to the position of the target individual before a treatment activity or when a treatment activity is started, and the initial position state and a current position state of the target individual during the treatment activity correspond to each other (the two positions may be, for example, represented by the coordinates of the movement of a movable hospital bed relative to a bottom support structure). During image guidance, an image acquired in real time can be compared with the reference 3D image, so as to provide information required for a medical activity, for example, a derivation between a focus position of a treatment beam and a position of a target volume during the radiotherapy, or whether a part to be excised has moved in a surgery, or the like.

As can be seen, according to the embodiments of the present disclosure, through the 3D-3D registration between the MR image and the reference 3D image, a region range of an object of interest in an MR image which has a very high accuracy is marked in the reference 3D image. As such, the image-guided process in which the reference 3D image is adopted to characterize the initial position state can also have the benefits provided by the MRI which has a high contrast resolution on soft tissues. In this way, the MRI can be introduced into the real-time image guidance, and the advantages of the MRI technique can also benefit the performing of real-time image guidance.

Figure 2:
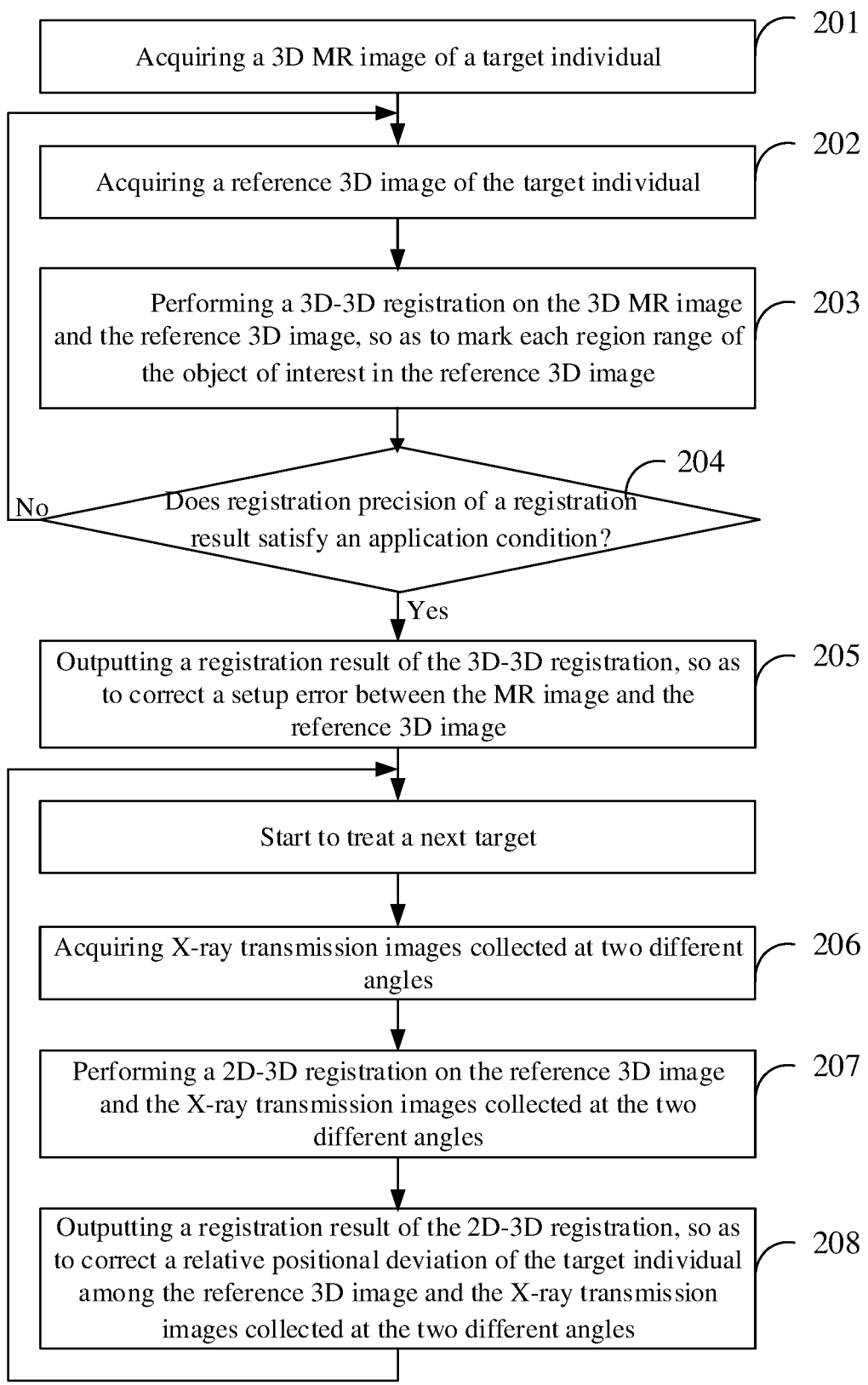
FIG. 2 is a schematic flowchart showing a method for performing image guidance according to another embodiment of the present disclosure.

IGRT of lung cancer is taken as an example. FIG. 2 is a schematic flowchart of a method for performing image guidance according to another embodiment of the present disclosure. Referring to FIG. 2, the method is performed by radiotherapy equipment. The method includes the following steps.

In step 201, a 3D MR image of a target individual is acquired.

In an example, before radiotherapy, a medical person operates MRI equipment to perform 3D imaging on the chest of the target individual (a patient with lung cancer), so as to acquire a 3D MR image of the chest of the target individual. Then, the MR image is transmitted to a computer based on a connection between equipment. Subsequently, the medical person operates the computer to draw various focus regions in the MR image for use as the at least one region range of object of interest as marked in the foregoing 3D MR image. In step 201, based on the connection between equipment, a control system of the radiotherapy equipment receives the MR image in which various focus regions have been marked from the computer device, to complete the 3D MR image.

In step 202, a reference 3D image of the target individual is acquired.

In an example, before radiotherapy, the medical person performs pre-treatment setup on the target individual, for example, the medical person may change the posture and position of the target individual with the guidance of a laser line emitted by the radiotherapy equipment, so as to align the laser line with a corresponding position of the target individual. After the setup is completed, the medical person operates a CBCT system in the radiotherapy equipment, to perform CBCT imaging on the chest of the target individual. In step 202, after the imaging is completed, the control system of the radiotherapy equipment receives acquired CBCT image data, so as to acquire 3D volume data of the chest of the target individual through the 3D reconstruction, thereby obtaining the reference 3D image. It should be understood that, because a cone beam artifact may be present in the 3D-reconstruction of the CBCT image, at the stage of selecting an ROI during the 3D reconstruction, the radiotherapy equipment may output a prompt to the user to guide the user to remove the part of the reference 3D image having an image artifact (for example, a start part and an end part of the CBCT image), to help improve the accuracy of the CBCT image.

In step 203, a 3D-3D registration is performed on the 3D MR image and the reference 3D image, so as to mark each region range of the object of interest in the reference 3D image.

In an example, after acquiring the MR image and the reference 3D image, the radiotherapy equipment performs a 3D-3D image registration on the MR image and the reference 3D image. In an example, the 3D-3D image registration includes seeking an optimal transform relationship between the MR image and the reference 3D image in an iterative fashion, and using a determining whether to continue with iteration. The iteration is stopped when the registration precision reaches a designated level, and the acquired transform relationship is outputted as the registration result. Based on the transform relationship of the registration result, each region range of the object of interest in the MR image can be transformed into a respective region range of the object of interest in the reference 3D image, thereby completing the process of marking each region range of the object of interest in the reference 3D image.

In step 204, the reference 3D image of the target individual is reacquired in response to that registration precision of a registration result does not meet an application condition.

In an example, a maximum iteration number is set in the iteration process. When the maximum iteration number is reached but the registration precision is still lower than the designated level, the iteration is stopped, and the process returns to step 202 to reacquire the reference 3D image. In this example, the application condition is that "the registration precision reaches the designated level". The application condition can be set according to an actual application requirement. It should be understood that in a case that the number of iterations reaches the maximum iteration number but the registration precision is still lower than the designated level, it may be considered that, at this time, the difference between the reference 3D image and the MR image is too large, making it difficult to find an appropriate image transform relationship. Therefore, in such case, by reacquiring the reference 3D image and repeating the intermediate processes, the registration precision can be ensured while improving the accuracy of each region range of the object of interest in the reference 3D image.

In step 205, a registration result of the 3D-3D registration is outputted, so as to correct a setup error between the MR image and the reference 3D image.

In an example, in a case that the registration precision satisfies the application condition, the radiotherapy equipment may output the registration result, to prompt the medical person to move the bed, so as to correct the setup error between the reference 3D image and the MR image. Generally, the MR image is regarded as being standardized. Therefore, the MR image can represent a standard setup position. Therefore, in the case that the registration precision between the reference 3D image and the MR image satisfies the application condition, the registration result can be regarded as representing a deviation between a current setup position and the standard setup position, thus the standard setup position can be accomplished through moving the bed. Based on the foregoing process, the setup error can be reduced.

After the foregoing process, the preparations before radiotherapy has been completed, and it may start to sequentially treat the respective targets. Steps 206 to 208 are steps performed in a process of treating each target. In this process:

In step 206, X-ray transmission images collected at two different angles are acquired.

In an example, the radiotherapy equipment may be operated by the medical person to perform X-ray transmission imaging at two different angles (the two angles are respectively referred to as the first angle and the second angle) on the chest of the target individual, to acquire a group of two X-ray transmission images. The two X-ray transmission images in one group jointly characterize a current position state of the target individual.

In step 207, a 2D-3D registration is performed on the reference 3D image and the X-ray transmission images collected at the two different angles.

In an example, the process of the 2D-3D registration includes: based on the reference 3D image and using a ray casting algorithm, generating digitally reconstructed radiographs (DRR) at the first angle and the second angle respectively; comparing the acquired group of two DRRs with the group of two X-ray transmission images; optimizing parameters of the spatial transformation based on the comparison result, to regenerate a group of two DRRs according to the optimized parameters; repeating the foregoing process (an iteration process); and outputting optimized parameters of the spatial transformation as the registration result of the 2D-3D registration when an end condition is satisfied.

In step 208, a registration result of the 2D-3D registration is outputted, so as to correct a relative positional deviation of the target individual among the reference 3D image and the X-ray transmission images collected at the two different angles.

It should be understood that the relative positional deviation may originate from an overall movement of the target individual within a time period between the moment of photographing the reference 3D image and the moment of photographing the two X-ray transmission images, or may originate from the movement of the internal tissue of the target individual relative to the target individual. The relative positional deviation is not limited thereto. For the application scenario of radiotherapy, the relative positional deviation specifically refers to a deviation of a current position of a target volume relative to the reference position (that is, the position of the target volume determined based on the reference 3D image). Certainly, for an application scenario other than radiotherapy, the relative positional deviation may have different meanings, and the objective of outputting the registration result of the 2D-3D registration may not be limited to correcting the relative positional deviation (which may be, for example, tracking the movement of an object inside the target individual, or acquiring the real excision condition of a part to be excised).

In an example, the radiotherapy equipment may output a registration result of the 2D-3D registration to the medical person, to represent the deviation between a focus position of a treatment beam and the position of the target volume at a current moment. On this basis, when the deviation is greater than a predetermined threshold, the radiotherapy equipment may be operated by the medical person to cause the bed to move, according to the registration result, to correct this deviation. When the deviation is greater than or equal to the predetermined threshold, the treatment can be continued without needing to move the bed. It should be understood that the predetermined threshold can be determined according to an actual application scenario and an application requirement.

Treatment process on each target can be sequentially completed according to the process of steps 206 to 208, so as to eventually complete the whole image guidance process. As can be seen, according to the embodiments of the present disclosure, through the 3D-3D registration between the MR image and the reference 3D image, a region range of an object of interest in an MR image which has a very high accuracy is marked in the reference 3D image. As such, the image-guided process in which the reference 3D image is adopted to characterize the initial position state can also have the benefits provided by the MRI which has a high contrast resolution on soft tissues. In this way, the MRI can be introduced into the real-time image guidance, and the advantages of the MRI technique can also benefit the performing of real-time image guidance.

As a comparative example, in a method for performing image guidance, the method is based on FIG. 2 but steps 201, 203, 204, and 205 are omitted, as such, a reference 3D image acquired through the 3D reconstruction of CBCT image data is directly used for performing the image guidance. It can be seen that, on one hand, the respective region ranges of the object of interest can hardly be accurately positioned in the reference 3D image, which may bring certain difficulty and uncertainty to the radiotherapy; on the other hand, the initial setup error cannot be corrected, which may probably affect the accuracy of radiotherapy. In contrast, in the embodiments of the present disclosure, an MR image can be used to provide accurate positioning for the respective region ranges of the object of interest, and can help correct the initial setup error, thereby making the radiotherapy more accurate and simpler.

In addition, it needs to be noted that based on any foregoing example, it is not feasible to directly use an MR image to replace the CBCT image to function as a reference 3D image. The reason mainly lies in that, on the basis of 3D volume data acquired through CBCT, the ray transmission algorithm can simulate the attenuation and exposure processes of X rays passing through different tissues and organs of a human body. The acquired CT value is represented by a ratio of the attenuation of X rays in tissue to the attenuation of X rays in water:

$$\mu = (CT/1000+1) \cdot \mu_{water} \cdot F.$$

In this formula, F is a transformation factor, $\mu$ is an attenuation coefficient of X rays in tissue, and $\mu_{water}$ is an attenuation coefficient of X rays in water. On this basis, an accumulated attenuation parameter of each ray passing through the 3D volume data can be calculated based on the process of X rays passing through 3D volume data formed from different CT values:

$$I = I_0 \cdot e^{-\Sigma \mu_i l_i}.$$

In this formula, $I_0$ is initial intensity of X rays, $\mu_i$ is a linear attenuation coefficient of tissue i, $l_i$ is a length by which X rays pass through the tissue i, and I is the intensity of the X rays after passing through the 3D volume data. Based on the foregoing relationship, by converting I into image grayscale values, the 3D-reconstructed CBCT image can be transformed into a 2D DRR. However, in a case of an MR image, what is reflected by the MR image is the hydrogen content in different tissues of a human body. MRI values of an image does not have a similar relationship with the attenuation coefficients of tissues, as what the CT values and the attenuation coefficients of tissues have. Even if the accumulated attenuation parameter of each ray is calculated according to the above calculation method by simulating rays passing through the 3D volume data formed from MRI values, the acquired values also cannot correctly reflect density attenuation information of different tissues, and thus the MR image and the X-ray transmission images acquired in real time cannot be accurately registered.

Based on the foregoing reasons, the MRI generally cannot be applied to real-time image guidance, and the effect of high contrast resolution on soft tissues of the MRI cannot be used to enhance the effect of image guidance. However, in the embodiments of the present disclosure, a 3D-3D registration between an MR image and a reference 3D image is used in turn, such that the advantages of MRI can be indirectly applied to real-time image guidance via the reference 3D image. In this way, the real-time image guidance does not need to perform repetitive and numerous time-consuming imaging processes of an MRI, but can share the benefits provided by the advantages of MRI, thus real-time image guidance with a better effect can be achieved.

Figure 3:
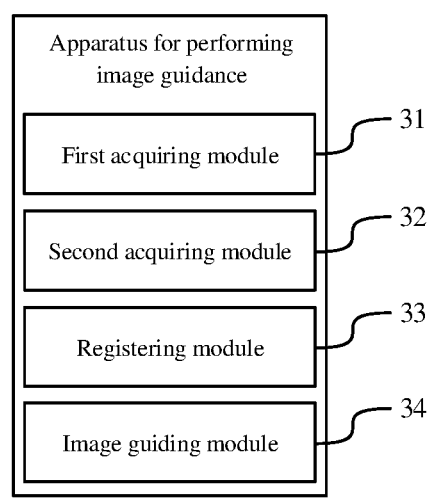
FIG. 3 is a structural block diagram of an apparatus for performing image guidance according to an embodiment of the present disclosure.

FIG. 3 is a structural block diagram of an apparatus for performing image guidance according to an embodiment of the present disclosure. Referring to FIG. 3, the apparatus for performing image guidance includes:

a first acquiring module 31, configured to acquire a 3D MR image of a target individual, where at least one region range of an object of interest is marked in the 3D MR image;

a second acquiring module 32, configured to acquire a reference 3D image of the target individual, where the reference 3D image is a 3D-reconstructed CT image;

a registering module 33, configured to perform a 3D-3D registration on the 3D MR image and the reference 3D image, so as to mark each region range of the object of interest in the reference 3D image; and an image guiding module 34, configured to perform image guidance on the basis that the reference 3D image is adopted to characterize an initial position state.

In a possible implementation, the apparatus further includes:

an outputting module, configured to output, before the image guidance is performed on the basis that the reference 3D image is adopted to characterize the initial position state, a registration result of the 3D-3D registration, so as to correct a setup error between the MR image and the reference 3D image.

In a possible implementation, the second acquiring module 32 is further configured to reacquire, before the registration result of the 3D-3D registration is outputted and in response to that registration precision of the registration result does not satisfy an application condition, the reference 3D image of the target individual.

In a possible implementation, the reference 3D image is a 3D-reconstructed CBCT image; and the apparatus further includes:

an image processing module, configured to remove, before the 3D-3D registration is performed on the 3D MR image and the reference 3D image, artifacts in the reference 3D image.

In a possible implementation, the image guiding module 34 includes:

an acquiring unit, configured to acquire X-ray transmission images collected at two different angles;

a registering unit, configured to perform a 2D-3D registration on the reference 3D image and the X-ray transmission images collected at the two different angles; and an outputting unit, configured to output a registration result of the 2D-3D registration, so as to correct a relative positional deviation of the target individual among the reference 3D image and the X-ray transmission images collected at the two different angles.

It should be understood that according to the optional implementations of the method for performing image guidance described above, the apparatus for performing image guidance can implement any foregoing method for performing image guidance by using a corresponding structure and configuration. Specific details are not described again.

In an example corresponding to FIG. 3, the apparatus for performing image guidance is embodied in the form of functional units/functional modules. The "unit/module" herein may be an application specific integrated circuit (ASIC), a processor executing one or more software or firmware programs and a memory, an integrated logic circuit, and/or any other device that can provide the foregoing functions. For example, at least some functions of at least one of the units and modules can be implemented by a processor executing program code stored in the memory.

Figure 4:
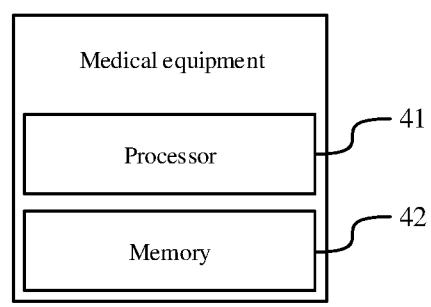
FIG. 4 is a structural block diagram of medical equipment according to an embodiment of the present disclosure.

FIG. 4 is a structural block diagram of medical equipment according to an embodiment of the present disclosure. Referring to FIG. 4, the medical equipment includes a processor 41 and a memory 42. The memory 42 stores program instructions therein. The processor 41 is configured to call the program instructions in the memory 42 to execute any foregoing method for performing image guidance.

The processor 41 may include a central processing unit (CPU, a single core or multi-core CPU), a graphics processing unit (GPU), a microprocessor, an application-specific integrated circuit (ASIC), a digital signal processor (DSP), a digital signal processing device (DSPD), a programmable logic device (PLD), a field-programmable gate array (FPGA), a controller, a microcontroller, or a plurality of integrated circuits configured to control the execution of a program.

The memory 42 may include a read-only memory (ROM) or other types of static storage device that may store static information and instructions, a random access memory (RAM) or other types of dynamic storage device that may store information and instructions, or may include an electrically erasable programmable read-only memory (EE-PROM), a compact disc read-only memory (CD-ROM) or other optical disc storage, a disc storage (including a compact disc, a laser disc, a disc, a digital versatile disc, a blue-ray disc, or the like), a magnetic disk storage medium or other magnetic storage device, or any other medium that can be configured to carry or store expected program code in the form of instructions or a data structure and can be accessed by a computer, but is not limited thereto. The memory may be disposed independently or may be integrated with a processor.

In specific implementations, as an embodiment, the processor 41 may include one or more CPUs. In specific implementations, as an embodiment, the medical equipment may include a plurality of processors. Each of these processors may be a single-CPU processor or may be a multi-CPU processor. The processor herein may be one or more devices, circuits, and/or processing cores configured to process data (for example, computer program instructions).

The medical equipment may include a general-purpose computer device or a special-purpose computer device. In specific implementations, the medical equipment may be any electronic device that requires medical image registration, for example, radiotherapy equipment, an image-guided medical equipment, an operating table, or the like. The computer device may be a desktop computer, a portable computer, a network server, a personal digital assistant (PDA), a mobile phone, a tablet computer, a wireless terminal device, a communication device, an embedded device or a device with a similar structure.

An embodiment of the present disclosure further provides a computer-readable storage medium, configured to store a computer program used for any foregoing method for performing image guidance. The computer program includes program instructions. The stored program is executed to implement any foregoing method for performing image guidance provided in the present disclosure.

A person skilled in the art should understand that the present disclosure may be provided as a method, an apparatus (a device) or a computer program product. Therefore, the present disclosure may adopt embodiments using only hardware, embodiments using only software, or embodiments using a combination of software and hardware. Moreover, the present disclosure may adopt a form of a computer program product that is implemented on one or more computer-usable storage media (including but not limited to a disk memory, a CD-ROM, an optical memory, and the like) that include computer usable program codes. The computer program is stored/distributed in an appropriate medium, and is provided together with other hardware or used as a part of hardware, or may use other distribution form, for example, the internet or other wired or wireless telecommunication system.

The present disclosure is described with reference to the flowcharts and/or block diagrams of the method, the apparatus (device), and the computer program product in the embodiments of the present disclosure. It should be understood that computer program instructions may be used to implement each process and/or each block in the flowcharts and/or the block diagrams and a combination of a process and/or a block in the flowcharts and/or the block diagrams. These computer program instructions may be provided for a general-purpose computer, a dedicated computer, an embedded processor, or a processor of any other programmable data processing device to generate a machine, such that the instructions executed by a computer or a processor of any other programmable data processing device generate an apparatus for implementing a specific function in one or more processes in the flowcharts and/or in one or more blocks in the block diagrams.

These computer program instructions may be stored in a computer-readable memory that can instruct the computer or any other programmable data processing device to work in a specific fashion, such that the instructions stored in the computer-readable memory generate an artifact that includes an instruction apparatus. The instruction apparatus implements a specific function in one or more processes in the flowcharts and/or in one or more blocks in the block diagrams.

These computer program instructions may be loaded onto a computer or another programmable data processing device, such that a series of operations and steps are performed on the computer or the another programmable device, thereby generating computer-implemented processing. Therefore, the instructions executed on the computer or the another programmable device provide steps for implementing a specific function in one or more processes in the flowcharts and/or in one or more blocks in the block diagrams.

Described above are merely embodiments of the present disclosure and are not intended to limit the present disclosure. Within the spirit and principles of the present disclosure, any modifications, equivalent substitutions, improvements, and the like are within the protection scope of the present disclosure.

What is claimed is:

1. A method for performing image guidance, comprising:
   acquiring a 3D magnetic resonance (MR) image of a target individual, wherein at least one region of interest is marked in the 3D MR image;
   acquiring a reference 3D image of the target individual, wherein the reference 3D image is a 3D-reconstructed computed tomography (CT) image;
   performing a 3D-3D registration on the 3D MR image and the reference 3D image to transform the at least one region of interest in the 3D MR image into at least one region of interest in the reference 3D image, so as to mark each region of interest in the reference 3D image; and
   performing image guidance on a basis that the reference 3D image is adopted to characterize an initial position state of the target individual, at least one region of interest marked in the reference 3D image and transformed from the at least one region of interest in the 3D MR image being used to determine a reference position of a target volume at a start moment of a treatment activity.

2. The method according to claim 1, wherein before performing the image guidance on the basis that the reference 3D image is adopted to characterize the initial position state, the method further comprises:
   outputting a registration result of the 3D-3D registration, so as to correct a setup error between the MR image and the reference 3D image.

3. The method according to claim 2, wherein before outputting the registration result of the 3D-3D registration, so as to correct the setup error between the MR image and the reference 3D image, the method further comprises:
   reacquiring the reference 3D image of the target individual in response to a registration precision of the registration result not satisfying an application condition.

4. The method according to claim 1, wherein the reference 3D image is a 3D-reconstructed cone beam computed tomography (CBCT) image; and wherein before performing the 3D-3D registration on the 3D MR image and the reference 3D image to transform the at least one region of interest in the 3D MR image into at least one region of interest in the reference 3D image, so as to mark each region of interest in the reference 3D image, the method further comprises:
   removing artifacts in the reference 3D image.

5. The method according to claim 4, wherein removing the artifacts in the reference 3D image comprises:
   removing cone beam computed tomography (CBCT) images having artifacts from the CBCT images.

6. The method according to claim 1, wherein performing the image guidance on the basis that the reference 3D image is adopted to characterize the initial position state comprises:
   acquiring X-ray transmission images collected at two different angles;
   performing a 2D-3D registration on the reference 3D image and the X-ray transmission images collected at the two different angles; and
   outputting a registration result of the 2D-3D registration, so as to correct a relative positional deviation of the target individual among the reference 3D image and the X-ray transmission images collected at the two different angles.

7. Medical equipment, comprising a processor and a memory storing program instructions therein, wherein the processor is configured to execute the program instructions in the memory to execute the method as defined in claim 1.

8. The medical equipment according to claim 7, wherein the method further comprises reacquiring, before a registration result of the 3D-3D registration is outputted, the reference 3D image of the target individual in response to a registration precision of the registration result not satisfying an application condition.

9. The medical equipment according to claim 7, wherein the reference 3D image is a 3D-reconstructed cone beam computed tomography (CBCT) image; and wherein the method further comprises:
removing artifacts in the reference 3D image before the 3D-3D registration is performed on the 3D MR image and the reference 3D image.

10. The medical equipment according to claim 7, wherein performing the image guidance on the basis that the reference 3D image is adopted to characterize the initial position state comprises:
acquiring X-ray transmission images collected at two different angles;
performing a 2D-3D registration on the reference 3D image and the X-ray transmission images collected at the two different angles; and
outputting a registration result of the 2D-3D registration, so as to correct a relative positional deviation of the target individual among the reference 3D image and the X-ray transmission images collected at the two different angles.

11. An apparatus for performing image guidance, comprising: a processor and a memory storing program instructions therein, wherein the processor is configured to execute the program instructions in the memory to perform a method for performing image guidance, wherein the method comprises:
acquiring a 3D magnetic resonance (MR) image of a target individual, wherein at least one region of interest is marked in the 3D MR image;
acquiring a reference 3D image of the target individual, wherein the reference 3D image is a 3D-reconstructed computed tomography (CT) image;
performing a 3D-3D registration on the 3D MR image and the reference 3D image to transform the at least one region of interest in the 3D MR image into at least one region of interest in the reference 3D image, so as to mark each region of interest in the reference 3D image; and
performing image guidance on a basis that the reference 3D image is adopted to characterize an initial position state of the target individual, at least one region of interest marked in the reference 3D image and transformed from the at least one region of interest in the 3D MR image being used to determine a reference position of a target volume at a start moment of a treatment activity.

12. The apparatus according to claim 11, wherein the method further comprises:
outputting, before the image guidance is performed on the basis that the reference 3D image is adopted to characterize the initial position state, a registration result of the 3D-3D registration, so as to correct a setup error between the MR image and the reference 3D image.

13. The apparatus according to claim 12, wherein the method further comprises reacquiring, before the registration result of the 3D-3D registration is outputted, the reference 3D image of the target individual in response to a registration precision of the registration result not satisfying an application condition.

14. The apparatus according to claim 11, wherein the reference 3D image is a 3D-reconstructed cone beam computed tomography (CBCT) image; and wherein the method further comprises:
removing artifacts in the reference 3D image before the 3D-3D registration is performed on the 3D MR image and the reference 3D image.

15. The apparatus according to claim 14, wherein removing the artifacts in the reference 3D image comprises:
removing cone beam computed tomography (CBCT) images having artifacts from the CBCT images.

16. The apparatus according to claim 11, wherein performing the image guidance on the basis that the reference 3D image is adopted to characterize the initial position state comprises:
acquiring X-ray transmission images collected at two different angles;
performing a 2D-3D registration on the reference 3D image and the X-ray transmission images collected at the two different angles; and
outputting a registration result of the 2D-3D registration, so as to correct a relative positional deviation of the target individual among the reference 3D image and the X-ray transmission images collected at the two different angles.

17. A non-transitory computer-readable storage medium, storing a computer program therein, wherein the computer program comprises program instructions, and the program instructions, when executed by a processor, causes the processor to perform a method for performing image guidance comprising:
acquiring a 3D magnetic resonance (MR) image of a target individual, wherein at least one region of interest is marked in the 3D MR image;
acquiring a reference 3D image of the target individual, wherein the reference 3D image is a 3D-reconstructed computed tomography (CT) image;
performing a 3D-3D registration on the 3D MR image and the reference 3D image to transform the at least one region of interest in the 3D MR image into at least one region of interest in the reference 3D image, so as to mark each region of interest in the reference 3D image; and
performing image guidance on a basis that the reference 3D image is adopted to characterize an initial position state of the target individual, at least one region of interest marked in the reference 3D image and transformed from the at least one region of interest in the 3D MR image being used to determine a reference position of a target volume at a start moment of a treatment activity.

18. The non-transitory computer-readable storage medium according to claim 17, wherein the method further comprises:
outputting, before the image guidance is performed on the basis that the reference 3D image is adopted to characterize the initial position state, a registration result of the 3D-3D registration, so as to correct a setup error between the 3D MR image and the reference 3D image.

19. The non-transitory computer-readable storage medium according to claim 18, wherein the method further comprises reacquiring, before the registration result of the 3D-3D registration is outputted, the reference 3D image of the target individual in response to a registration precision of the registration result not satisfying an application condition.

20. The non-transitory computer-readable storage medium according to claim 17, wherein the reference 3D image is a 3D-reconstructed cone beam computed tomography (CBCT) image; and wherein the method further comprises:
   removing artifacts in the reference 3D image before the 3D-3D registration is performed on the 3D MR image and the reference 3D image.

\* \* \* \* \*